United States Patent
Centola et al.

(10) Patent No.: US 10,428,130 B2
(45) Date of Patent: Oct. 1, 2019

(54) PURIFICATION OF BONE MORPHOGENETIC PROTEINS (BMPS)

(71) Applicant: ISTITUTO BIOCHIMICO ITALIANO GIOVANNI LORENZINI S.P.A., Aprilia (IT)

(72) Inventors: Fabio Centola, Rome (IT); Leonardo Sibilio, Rome (IT)

(73) Assignee: ISTITUTO BIOCHIMICO ITALIANO GIOVANNI LORENZINI S.P.A., Aprilia (IT)

(*) Notice: Subject to any disclaimer, the term of this patent is extended or adjusted under 35 U.S.C. 154(b) by 0 days.

(21) Appl. No.: 15/559,318

(22) PCT Filed: Mar. 16, 2016

(86) PCT No.: PCT/EP2016/055683
§ 371 (c)(1),
(2) Date: Sep. 18, 2017

(87) PCT Pub. No.: WO2016/146680
PCT Pub. Date: Sep. 22, 2016

(65) Prior Publication Data
US 2018/0111973 A1    Apr. 26, 2018

(30) Foreign Application Priority Data

Mar. 17, 2015 (IT) .............. F12015A0074

(51) Int. Cl.
*C07K 14/51* (2006.01)
*C07K 14/495* (2006.01)
*C07K 1/16* (2006.01)

(52) U.S. Cl.
CPC .......... *C07K 14/51* (2013.01); *C07K 1/165* (2013.01); *C07K 14/495* (2013.01)

(58) Field of Classification Search
None
See application file for complete search history.

(56) References Cited

U.S. PATENT DOCUMENTS

| | | | | |
|---|---|---|---|---|
| 5,756,457 A | * | 5/1998 | Wang | A61K 38/1875 424/422 |
| 2004/0115785 A1 | * | 6/2004 | Fong | C07K 16/06 435/188.5 |

FOREIGN PATENT DOCUMENTS

| | | |
|---|---|---|
| EP | 2407477 A1 | 1/2012 |
| WO | 91/04267 A1 | 4/1991 |

OTHER PUBLICATIONS

International Search Report and Written Opinion for corresponding Application No. PCT/EP2016/055683 (dated Jun. 16, 2016).

* cited by examiner

*Primary Examiner* — Elizabeth C. Kemmerer
(74) *Attorney, Agent, or Firm* — Pepper Hamilton LLP

(57) ABSTRACT

The present invention relates to a method for purifying a protein belonging to the transforming growth factor-β (TGF-β) superfamily, said method comprising subjecting a cell culture medium containing the protein to a Hydrophobic Charge 5 Interaction Chromatography (HCIC).

11 Claims, 1 Drawing Sheet

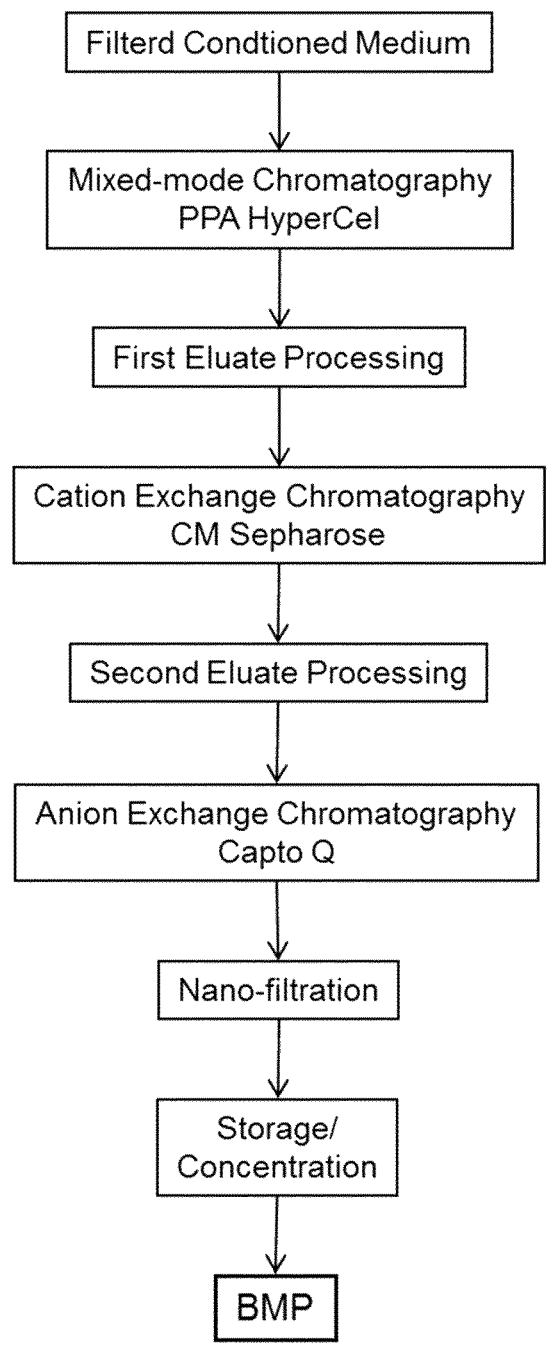

PURIFICATION OF BONE MORPHOGENETIC PROTEINS (BMPS)

This application is a national stage application under 35 U.S.C. § 371 of PCT Application No. PCT/EP2016/055683, filed 16 Mar. 2016, which claims priority of Italy Application No. FI2015A000074, filed 17 Mar. 2015, which are hereby incorporated by reference in their entirety.

FIELD OF THE INVENTION

The present invention relates to a method for purifying a protein belonging to the transforming growth factor-β (TGF-β) superfamily, preferably a bone morphogenetic protein (BMP), and more preferably a bone morphogenetic protein 4 (BMP-4). This invention is focused on the purification of a BMPs from mammalian cells.

STATE OF THE ART

It has been reported that BMPs regulate the growth and differentiation of cells such as osteogenic cells, and particularly BMP-2, BMP-4, BMP-5, BMP-6, BMP-7 and BMP-8 are growth and differentiation factors that can induce ectopic bone formation alone in vitro and in vivo. Also, BMP-2 can direct the development of neural crest cells into neural phenotypes, and BMP-4 and BMP-7 can induce a sympathetic adrenergic phenotype. It has been reported that a heterodimer composed of BMP-4 and BMP-7 is a potent inducer of mesoderm (see A. Suzuki, E. Kaneko, J. Maeda and N. Ueno, "Mesoderm induction by BMP-4 and -7 heterodimers," Biochem. Biophys. Res. Commun., vol. 232, pp. 153-156, March 1997).

Particularly, it is known in the art that BMPs, belonging to the TGF-β superfamily of proteins, plays an important role in the development of bone and cartilage, and potentially induce osteoblastic differentiation of a variety of cell types. Also, BMPs acts to stimulate bone production, and products that induce new bone formation by implanting BMP-2 into collagen sponges are being marketed.

Bone morphogenetic proteins (BMPs) may be produced in cultures (yeast, *E. Coli*, and mammalian cells) transformed with an expression vector containing the corresponding DNA. The cloning and expression of the transforming growth factor-β superfamily have been previously reported in several patents (such as for example U.S. Pat. No. 5,700,911, US2004/0009916 and U.S. Pat. No. 5,618,924).

The production of recombinant proteins in host cells allows high production level and, in many cases, it is possible to secrete the protein. For this reason the goal of a purification protocol is the isolation of the protein from the culture media. Typically, the culture media contains nutrients (vitamins, amino acids, co-factors and minerals) and additional growth-factors and supplements as the insulin. Moreover, even though the protein is expressed in high level, the endogenous proteins of the cells, well known as Host Cell Proteins, are also expressed and secreted in the culture medium. For this reason the concentration of the recombinant protein is usually very low.

The endogenous proteins could possess the same characteristics, in terms of isoelectric point (pI), molecular weight, amino acid composition very similar to the target protein increasing dramatically the efforts that should be made to separate the protein of interest from the contaminants.

In addition to the difficulties discussed above, it is possible that in the culture medium there are some additives that induces post-translational modifications or degradation of the product which potentially decrease the biological activity of the product as well as have toxic effects. These modified proteins must be removed, but their characteristics are obviously very almost the same of the product of interest representing one of the biggest challenge of the purification.

Where the purification is highly challenging, the proteins could be purified by affinity chromatography. Even though this kind of chromatography is a powerful step to obtain a highly purified product, the specifications of purity, needed for any clinical trial, are never satisfied. For this reason the affinity chromatography must be associated to one or more chromatographic or physical steps.

In many case it is observed that some proteins, that show a net charge in some region, could bind some Host Cell Proteins by ionic bonds. These bonds cooperate together increasing drastically the total bond strength avoiding any possibility to dissociate the proteins, decreasing dramatically the purity of the final product. US2003/0036629 describes a method for purifying a TGF-6 superfamily protein in a solution (i.e. a cell culture medium treated with dextran sulfate) applying said solution to a heparin-like resin, eluting said heparin-like resin with a first eluant to form a first eluate, applying said first eluate to a Butyl Sepharose-like resin, eluting said Butyl Sepharose-like resin with a second eluant to form a second eluate containing said TGFβ superfamily protein.

EP2407477 describes a method for purifying a protein belonging to the transforming growth factor-β (TGF-β) superfamily, comprising the steps of:
a) pre-treating a solution containing the protein belonging to the TGF-β superfamily, in which the solution is concentrated using a cut-off membrane filter;
b) subjecting the solution obtained in step a) to hydrophobic interaction chromatography;
c) diafiltering the solution obtained in step b); and
d) subjecting the solution obtained in step c) to size exclusion chromatography.

Accordingly, there continues to exist a need in the art for protein purification methods that effectively overcome all of these difficulties. Aim of the present invention is therefore to provide a method, if not improved at least alternative and that could be performed in large scale, for purifying a protein belonging to the transforming growth factor-β (TGF-β) superfamily in order to obtain it with a pharmaceutical grade purity.

SUMMARY OF THE INVENTION

Subject-matter of the present invention is a method of purifying a secreted TGF-β superfamily protein, said method comprising (i) contacting a solution containing the secreted TGF-β superfamily protein with a Hydrophobic Charge Interaction Chromatography (HCIC) resin.

Surprisingly the HCIC step allows to obtain the TGF-β superfamily protein with high yield and high purity. The process according to the invention is easily scalable at industrial scale.

The HCIC step shows two important advantages compared to the methods previously reported in literature.

The first advantage is that the product is eluted in an acidic environment where the BMPs are usually very stable.

Moreover, because the protein is already in an acidic environment, it is easily possible to further decrease the pH with clearly advantage in terms of viral inactivation (MuLV).

The second advantage is that with this step, which is the first chromatographic step, it is possible to remove more than 98% of the total host proteins of the harvest, as shown by Bradford assay and the integration of chromatogram peaks at 280 nm.

BRIEF DESCRIPTION OF THE FIGURES

FIG. 1 shows a preferred embodiment of the process of the invention.

DETAILED DESCRIPTION OF THE INVENTION

According to the invention the secreted TGF-β superfamily protein is preferably a secreted BMP. As used herein, the term "BMP" includes all the BMPs secreted in the medium culture from any kind of cell (mammalian, yeast and bacteria) preferably from mammalian cells. According to the invention, preferably the BMP is BMP-4. Preferably method of the invention further comprising (ii) contacting the first eluate containing the secreted TGF-β superfamily protein with a cation-exchange chromatography resin for obtaining a second eluate containing the secreted TGF-β superfamily protein.

Preferably method according to any one of claims 1-2 further comprising contacting the second eluate containing the secreted TGF-β superfamily protein with a anion-exchange chromatography resin for obtaining the purified secreted TGF-β superfamily protein.

According to the invention the solution containing the secreted TGF-β superfamily protein, said solution being subjected to the HCIC step, is that obtained from a harvest cell culture medium, containing the protein of interest, which has been filtered and adjusted to pH 7.0-9.5 and a salt concentration of 250-800 mM; preferably pH is adjusted at pH 7.4-9.0 and a salt concentration of 400-600 mM. pH is preferably adjusted by addition to the filtered culture medium of NaOH 0.5-1.5M and preferably 1.0M.

Salt concentration is preferably adjusted by addition of NaCl or KCl in powder or in solution from 2M to 5M, preferably a solution of 5M, and preferably NaCl.

HCIC is based on the pH-dependent behavior of ionizable, dual-mode ligands. Adsorption is based on mild hydrophobic interaction and is achieved without addition of lyotropic or other salts. Desorption is based on charge repulsion. It is performed by reducing pH. Resins suitable for performing HCIC are known as mixed-mode resins. As used herein, the term "mixed-mode resin" includes all the resins containing a functional group which works by hydrophobic interaction to bind the proteins and works by a positive-positive repulsion interaction to dissociate the proteins. This invention can be performed with all the resins where the protein of interest in the culture medium binds the resin by an hydrophobic interaction and where the elution occurs by ionic interaction (positive-positive repulsion interaction). Resins suitable for HCIC according to the invention are the mixed-mode resins carrying as ligands n-hexylamine (HEA) or phenylpropylamine (PPA) or 4-Mercapto-Ethyl-Pyridine (4-MEP) such as those currently commercially available from PALL Corporation. The most preferred resins from PALL Corporation are those selected in the group consisting of PPA HyperCel™, HEA HyperCel™ and MEP HyperCel™; more preferably the PPA HyperCel™.

Before loading the solution containing the secreted TGF-beta protein, the HCIC resin is preferably conditioned with a conditioning buffer having pH 7.4-9.5, preferably 8.8-9.0 and a salt concentration of 50-800 mM. pH is obtained with a 10-250 mM concentration of a buffer selected in the group consisting of Phosphate buffer, Glycine buffer, tris(hydroximethyl)aminoethane (TRIS), Methyldiethanolamine buffer, bis-Trispropane buffer and Piperazine buffer; preferably TRIS buffer. The salt concentration is of NaCl or KCl, preferably NaCl. The salt concentration is preferably off 500 mM.

Subsequently to loading the HCIC resin is subjected to pH decreasing washings and the protein elution is carried out by a further pH decreasing.

Subsequent to loading the HCIC resin is preferably subjected to at least two washing steps performed respectively with a washing buffer (A) at neutral pH 6.5-7.5 and with a washing buffer (B) at pH 3.0-4.5 with a concentration included from 50 mM and 250 mM. The elution step is performed with an elution buffer (E1) having pH 2.5-3.5 and comprising Glycine at a concentration of 50 mM and 200 mM. The washing buffer (A), preferably, is a solution of sodium phosphate buffer, potassium phosphate buffer, TRIS buffer, bis-TRIS, HEPES buffer or MES buffer; preferably Sodium Phosphate buffer.

The washing buffer (B), preferably, is a solution of Sodium Acetate buffer, Sodium Phosphate buffer, Potassium Phosphate buffer, Lactic acid and Citric acid, from 10 mM to 500 mM, preferably Sodium Acetate buffer at 100 mM.

The elution Glycine buffer (E1) preferably comprises Glycine at a concentration of 100 mM and pH is 2.7.

With the elution Glycine buffer (E1) is obtained the first eluate containing the desired secreted TGF-β superfamily protein.

One more important novel and advantageous aspect of the present invention is the use of Glycine buffer instead of the buffers, usually acetate and citrate, suggested from the HCIC resin suppliers. There is no data in literature about the use of this buffer with this kind of resin. The use of the glycine buffer is very important because it works not in a classical way where the mechanism is the following: decreasing the pH, the net charge of stationary phase begins positive as well as the net charge of the protein, the consequent repulsive interaction produces the release of the protein. On the contrary, the glycine buffer shows an interaction with the stationary phase and, even before the pH is lower enough to have a repulsive interaction, the glycine displaces the protein which is then eluted.

Data reported in the present invention demonstrate that using the classical buffers, even at very low pH, the yield is very low and the process is not convenient in economic and process terms.

The first eluate is then preferably applied to a cation exchange column.

As used herein, the term cation exchange column includes all the columns having a negative charge moiety including those produced from PALL, Toyopearl, POROS, Fractogel and GE Healthcare, more preferably CM Sepharose from GE Healthcare. According to the invention the cation exchange resin is preferably a weak cation exchange resin.

Preferably, prior to contacting with the cation-exchange resin, the first eluate is subjected to a processing comprising a virus inactivation step by decreasing the pH until pH 2.0-2.5 with HCl from 0.5% to 2% v/v, leaving the solution from 1 min to 120 min HCl, and a subsequent step comprising the pH changing by adding the virus inactivated first eluate (i.e. the solution containing the desired secreted TGF-β superfamily protein) to a 20 mM-50 mM phosphate or sulfate solution having pH 7.2-7.6 and containing a surfactant.

The surfactant can be any known surfactant, preferably a polysorbate, as Tween 20 and Tween 80, more preferably Tween 20. Prior to the addition of the virus inactivated first eluate, the pH of the phosphate or sulfate solution must be included from 8.0 to 9.4. The virus inactivated first eluate is preferably added under stirring condition, form 200 to 400 rpm, more preferably 300 rpm, to the phosphate solution adding also a solution of NaOH, from 0.5 to 1.2M, to control the pH. The final pH is preferably 7.2-7.6.

The first eluate, preferably processed as above described, can be loaded onto the cation exchange column.

After loading of the cation exchange column can, preferably, be washed, without eluting the secreted TGF-β superfamily protein, with a washing buffer (C) at pH 7.2-9.0. The washing buffer (C) is a solution containing sodium or potassium phosphate, sodium or potassium chloride or sodium sulfate, HEPES, Bicine or TRIS at a concentration of 10 mM-200 mM. The washing buffer (C) can preferably also contain a surfactant, from 0.001% to 0.1%, and an amino acid with a positive net charge (preferably Arginine or Glycine) at a concentration lower than 250 mM. More preferably the washing buffer (C) contains 25 mM sodium phosphate at pH7.4 and 150 mM Arginine. If a higher purity level is needed, it is possible to operate a wash with buffer TRIS pH 8.9 from 10 mM to 100 mM, partially eluting BMPs. The washing buffer (C) can contains other salts as sodium chloride or potassium chloride, or other molecules as Arginine or Glycine to have a conductivity included from 2 mS/cm to 15 mS/cm. It is possible to achieve the pH 8.9, but in this case the conductivity must be lower than 5 mS/cm.

The elution of the secreted TGF-β superfamily protein from the cation-exchange column is preferably carried out with a eluent buffer (E2), buffered at pH 8.8-9.1. Suitable buffers for eluent buffer (E2) can be, for example TRIS, Bicine, N-Methyl diethanolamine, diethanolamine, more preferably TRIS, with any salts, for example NaCl, KCl, preferably NaCl, with a conductivity higher than 10 mS/cm and lower than 80 mS/cm. Elution buffer (E2) can contain salts, as sodium chloride or potassium chloride, or molecules as Arginine. The conductivity of the buffer must be included between 10 mS/cm and 50 mS/cm. More preferably the "elution solution 3" contains 50 mM TRIS pH 8.9 and 200 mM sodium chloride.

With the elution buffer (E2) the second eluate containing the secreted TGF-β superfamily protein is thus obtained.

The second eluate is then preferably processed by way of dilution or by diafiltration with any solution buffering at pH 8.5-9.0, until conductivity is ≤8 mS/cm. The diluting solution can contain any salts or molecule as sodium chloride, potassium chloride, Arginine and Glycine. More preferably the buffer is 50 mM TRIS pH 8.9 and 100 mM Arginine. The conductivity of the second eluate solution, after the dilution, must preferably be lower than 10 mS/cm.

The second eluate, preferably processed as above described, can be contacted to the anion-exchange column selected among all the resins, from any supplier, having a positive charge group.

As used herein, the term anion exchange column includes all the columns having a positive charge moiety including those produced from PALL, TOSOH (such as Toyopearl®), POROS®, Fractogel® and GE Healthcare, more preferably Capto Q from GE Healthcare. According to the invention, the anion exchange resin is preferably a strong anion exchange resin.

Subsequently to loading onto anion exchange resin, washing steps must be performed with—any solution buffering from 6.0 to 9.0, comprising 20-100 mM of a buffer selected in the group consisting of sodium phosphate, potassium phosphate, Histidine, HEPES, Bicine and TRIS. The washing buffers can contains other salts as sodium chloride or potassium chloride, or other molecules as Arginine or Glycine to have a conductivity included from 2 mS/cm to 10 mS/cm. More preferably the washing buffer (D) are three: the first one (D1) contains 50 mM TRIS at pH8.9 and 100 mM Arginine, the second one (D2) contains 25 mM sodium phosphate at pH 7.4 and the third one (D3) contains 25 mM sodium phosphate at pH 6.5 and 75 mM sodium chloride.

Elution of the secreted TGF-β superfamily protein from the anion exchange resin is preferably obtained using an elution buffer (E3) having pH 7.2-7.6 with a conductivity included of 20-26 mS/cm; preferably sodium and potassium phosphate and HEPES, more preferably the buffer is a PBS 1.5× pH 7.4, prepared as described in pharmacopeia. The elution with elution buffer (E3) provide a third eluate containing the desired secreted TGF-β superfamily protein.

The third eluate is preferably further filtered with a Planova 20N nano-filter and stored frozen at −80° C. Optionally it is possible to concentrate it by tangential flow filtration with a hollow-fiber cartridge or a cassette with a molecular weight gut-off of 10 KDa.

The process of the present invention allowed BMPs purification with high yield and purity. The effectiveness of the process is demonstrated by several analysis, from RP-HPLC to SEC-HPLC, from SDS-PAGE to HCP ELISA. According to a preferred embodiment of the invention the BMP-4 produced by CHO cells was isolated and obtained with a 99% HPLC purity with 0-2% of aggregates and <5000 ppm of other host cells proteins.

FIG. 1 provides an overview of the a preferred embodiment of the process of the invention. The order of the steps is presently preferred, but numerous variations and modifications are possible, for example in the order of the steps. Such modifications are within the present invention.

Any cells capable to produce a protein of a TGF-β superfamily may be used for producing the cell culture medium to be used as starting solution in the method of the present invention. CHO cells are the preferred for producing BMPs and particularly BMP4. Even though the medium can be supplemented with FBS, it is preferred to use serum-free medium to avoid any risk of introducing viruses and other deleterious agents.

CHO cells are known to release lipids, carbohydrates, nucleic acids and proteins, as well as C-type particles (defective retroviral-like particles). Therefore, the purification process plays a key role to remove or inactivate these contaminants, as well as to remove media components such as salts, amino acids, sugars and especially large polymers. The entire process has been developed to obtain a highly purified protein. In this sense also the other steps subsequent to the HCIC step show some advantages.

In the batch processing, before the cation-exchange chromatographic step, the use of Tween 20 has two advantages: the first is that it increases the solubility of the protein at almost neutral pH (7.2-7.6). This is very important because the BMPs show a very low solubility around the neutral pH.

The second advantage is that Tween 20 plays a role in the viral inactivation (MuLV). The weak cation exchange chromatography is a very known resin, but, in terms of present state of art of BMPs purification, it is never used at very basic condition. The BMPs are in fact eluted at pH8.9 where their solubility is higher than neutral pH. After this step the BMP purity is about 98% or higher.

Finally, the anion-exchange step is a polishing step where the BMP purity is increased to 99.5% or more.

In order to achieve this result the second eluate is processed with TRIS-Arginine buffer at basic pH. The basic pH maintains the protein soluble as well as the use of the Arginine. Moreover the Arginine avoids the aggregate formation and competes with any binding from the BMPs and the residual HCP (Host Cell Proteins).

The last advantage of the third chromatographic step is that the final elution buffer is the PBS 1.5× pH7.4, which is almost ready to be used in parental dosage, after a formulation and/or a dilution.

The process has got one more advantage, compared those already reported in literature, it is very powerful to remove the MuLV virus, with a total log reduction higher than 20, as well as a log reduction of MMV virus higher than 8.

The examples below describe the present invention carried out for BMP4 purification, but the same process can be used with similar results for all the TGF-β proteins superfamily and particularly for Bone Morphogenetic proteins family. The following examples illustrate practice of the invention and are for illustrative purpose only.

EXPERIMENTAL SECTION

Examples Mixed-Mode Column

The protein is secreted into the culture medium at almost neutral pH. After the removal of cells, the medium must be processed in order to adjust the pH where needed and the salt concentration.

Example 1

MEP HyperCel is conditioned with 3CV (column Volume) of 50 mM Sodium Phosphate buffer at pH 7.4 and 500M NaCl at 300 cm/h. The culture medium (20-30CV) is further loaded at 152 cm/h. the column is then washed with the equilibrating buffer (5CV) and immediately after with 100 mM Sodium Acetate pH4.5 (5CV), 100 mM Sodium Acetate pH4.0 (5CV), 100 mM Sodium Acetate pH3.5 (5CV), 100 mM Sodium Acetate pH3.0 (5CV) at 300 cm/h. The product is then eluted at 300 cm/h with 100 mM Glycine HCl buffer at pH2.7.

Example 2

MEP HyperCel is conditioned with 3CV (column Volume) of 50 mM TRIS buffer at pH 8.2 and 500M NaCl at 300 cm/h. The culture medium (20-30CV) is further loaded at 152 cm/h. the column is then washed with the equilibrating buffer (5CV) and immediately after with 100 mM Sodium Acetate pH4.5 (5CV), 100 mM Sodium Acetate pH4.0 (5CV), 100 mM Sodium Acetate pH3.5 (5CV), 100 mM Sodium Acetate pH3.0 (5CV) at 300 cm/h. The product is then eluted at 300 cm/h with 200 mM Glycine HCl buffer at pH2.7.

Example 3

MEP HyperCel is conditioned with 3CV (column Volume) of 50 mM TRIS buffer at pH 8.8 and 500M NaCl at 300 cm/h. The culture medium (20-30CV) is further loaded at 152 cm/h. the column is then washed with the equilibrating buffer (5CV) and immediately after with 100 mM Sodium Acetate pH4.5 (5CV), 100 mM Sodium Acetate pH4.0 (5CV), 100 mM Sodium Acetate pH3.5 (5CV), 100 mM Sodium Acetate pH3.0 (5CV) at 300 cm/h. The product is then eluted at 300 cm/h with 200 mM Glycine HCl buffer at pH2.7.

Example 4

MEP HyperCel is conditioned with 3CV (column Volume) of 50 mM TRIS buffer at pH 8.8 and 500M NaCl at 300 cm/h. The culture medium (20-30CV) is further loaded at 300 cm/h. the column is then washed with the equilibrating buffer (5CV) and immediately after with 100 mM Sodium Acetate pH4.5 (5CV), 100 mM Sodium Acetate pH4.0 (5CV), 100 mM Sodium Acetate pH3.5 (5CV), 100 mM Sodium Acetate pH3.0 (5CV) at 300 cm/h. The product is then eluted at 300 cm/h with 200 mM Glycine HCl buffer at pH2.7.

Example 5

MEP HyperCel is conditioned with 3CV (column Volume) of 50 mM Sodium Phosphate buffer at pH 7.4 and 500M NaCl at 300 cm/h. The culture medium (20-30CV) is further loaded at 300 cm/h. the column is then washed with the equilibrating buffer (5CV) and immediately after with 100 mM Sodium Acetate pH4.0 (5CV), 100 mM Sodium Acetate pH3.0 and 1000 mM NaCl (5CV) at 300 cm/h. The product is then eluted at 300 cm/h with 200 mM Glycine HCl buffer at pH2.7.

TABLE 1

Summary of examples 1-5
Operating Parameters for MEP HyperCel column

| Purification Procedures | Example | Parameter | Target Range | % recovery BMF[VAL1] |
|---|---|---|---|---|
| Equilibration | 1, 2, 3, 4, 5 | Flow Rate | ≤300 cm/h | |
| | 1, 2, 3, 4, 5 | Conductivity | ≤50 mS/cm | |
| | 1, 5 | pH | 7.4 ± 0.2 | |
| | 2 | pH | 8.2 ± 0.2 | |
| | 3, 4 | pH | 8.8 ± 0.2 | |
| Load | 1, 2, 3 | Flow Rate | ≤152 cm/h | |
| | 4, 5 | Flow Rate | ≤300 cm/h | |
| | 1, 5 | pH | 7.4 ± 0.2 | |
| | 2 | pH | 8.2 ± 0.2 | |
| | 3, 4 | pH | 8.8 ± 0.2 | |
| | 1, 5 | | | <10 |
| | 2, 3, 4 | | | <5 |
| Wash | 1, 2, 3, 4, 5 | Flow Rate | ≤300 cm/h | |
| | 1, 2, 3, 4, 5 | | | <5 |
| Elution | 1, 2, 3, 4, 5 | Flow Rate | ≤300 cm/h | |
| | 1 | | | ≤50 |
| | 2, 3, 4, 5 | | | ≥85 |

Example 6

HEA HyperCel is conditioned with 3CV (column Volume) of 50 mM TRIS buffer at pH 8.8 and 500M NaCl at 300 cm/h. The culture medium (20-30CV) is further loaded at 152 cm/h. the column is then washed with the equilibrating buffer (5CV) and immediately after with 100 mM Sodium Acetate pH4.5 (5CV), 50 mM Sodium Acetate pH4.0 (5CV), 50 mM Sodium Acetate pH3.5 (5CV), 50 mM Sodium Acetate pH3.0 (5CV) at 300 cm/h. The product is then eluted at 300 cm/h with 100 mM Glycine HCl buffer at pH2.7. The example 6 is described in table 2.

TABLE 2

Summary of example 6
Operating Parameters for HEA HyperCel column

| Purification Procedures | Example | Parameter | Target Range | % recovery BMP |
|---|---|---|---|---|
| Equilibration | 6 | Flow Rate | ≤300 cm/h | |
| | 6 | Conductivity | ≤50 mS/cm | |
| | 6 | pH | 8.8 ± 0.2 | |
| Load | 6 | Flow Rate | ≤152 cm/h | |
| | 6 | pH | 8.8 ± 0.2 | |
| | 6 | | | <2 |
| Wash | 6 | Flow Rate | ≤300 cm/h | |
| | 6 | | | <20 |
| Elution | 6 | Flow Rate | ≤300 cm/h | |
| | 6 | | | ≥78 |

Example 7

PPA HyperCel is conditioned with 3CV (column Volume) of 50 mM TRIS buffer at pH 8.8 and 500M NaCl at 300 cm/h. The culture medium (20-30CV) is further loaded at 152 cm/h. the column is then washed with the equilibrating buffer (5CV) and immediately after with 100 mM Sodium Acetate pH4.5 (5CV), 50 mM Sodium Acetate pH4.0 (5CV), 50 mM Sodium Acetate pH3.5 (5CV), 50 mM Sodium Acetate pH3.0 (5CV) at 300 cm/h. The product is then eluted at 300 cm/h with 100 mM Glycine HCl buffer at pH2.7.

Example 8

PPA HyperCel is conditioned with 3CV (column Volume) of 50 mM TRIS buffer at pH 8.8 and 500M NaCl at 300 cm/h. The culture medium (20-30CV) is further loaded at 300 cm/h. the column is then washed with the equilibrating buffer (5CV) and immediately after with 100 mM Sodium Acetate pH4.5 (5CV), 50 mM Sodium Acetate pH4.0 (5CV), 50 mM Sodium Acetate pH3.5 (5CV), 50 mM Sodium Acetate pH3.0 (5CV) at 300 cm/h. The product is then eluted at 300 cm/h with 100 mM Glycine HCl buffer at pH2.7.

Example 9

PPA HyperCel is conditioned with 3CV (column Volume) of 50 mM TRIS buffer at pH 8.8 and 500M NaCl at 300 cm/h. The culture medium (20-30CV) is further loaded at 152 cm/h. the column is then washed with the equilibrating buffer (10CV) and immediately after with 100 mM Sodium Acetate pH4.0 (10CV), at 300 cm/h. The product is then eluted at 300 cm/h with 100 mM Glycine HCl buffer at pH2.7.

TABLE 3

Summary of examples 7-9
Operating Parameters for PPA HyperCel column

| Purification Procedures | Example | Parameter | Target Range | % recovery BMP |
|---|---|---|---|---|
| Equilibration | 7, 8, 9 | Flow Rate | 300 cm/h | |
| | 7, 8, 9 | Conductivity | 50 mS/cm | |
| | 7, 8, 9 | pH | 8.8 ± 0.2 | |
| Load | 7, 9 | Flow Rate | 152 cm/h | |
| | 8 | Flow Rate | 300 cm/h | |
| | 7, 8, 9 | pH | 8.8 ± 0.2 | |
| | 7, 8, 9 | | | <2 |
| Wash | 7, 8, 9 | Flow Rate | 300 cm/h | |
| | 7, 8 | | | <20 |
| | 9 | | | <2 |
| Elution | 7, 8, 9 | Flow Rate | 300 cm/h | |
| | 7, 8 | | | ≥75 |
| | 9 | | | ≥98 |

Example 10

PPA HyperCel is conditioned with 3CV (column Volume) of 50 mM TRIS buffer at pH 8.8 and 500M NaCl at 300 cm/h. The culture medium (20-30CV) is further loaded at 214 cm/h. the column is then washed with the equilibrating buffer (10CV) and immediately after with 100 mM Sodium Acetate pH4.0 (10CV), at 300 cm/h. The product is then eluted at 300 cm/h with 200 mM Glycine HCl buffer at pH3.5.

Example 11

PPA HyperCel is conditioned with 3CV (column Volume) of 50 mM TRIS buffer at pH 8.8 and 500M NaCl at 300 cm/h. The culture medium (20-30CV) is further loaded at 214 cm/h. the column is then washed with the equilibrating buffer (10CV) and immediately after with 100 mM Sodium Acetate pH4.0 (10CV), at 300 cm/h. The product is then eluted at 300 cm/h with 125 mM Glycine HCl buffer at pH3.5.

Example 12

PPA HyperCel is conditioned with 3CV (column Volume) of 50 mM TRIS buffer at pH 8.8 and 500M NaCl at 300 cm/h. The culture medium (20-30CV) is further loaded at 214 cm/h. the column is then washed with the equilibrating buffer (10CV) and immediately after with 100 mM Sodium Acetate pH4.0 (10CV), at 300 cm/h. The product is then eluted at 300 cm/h with 75 mM Glycine HCl buffer at pH3.5.

Example 13

PPA HyperCel is conditioned with 3CV (column Volume) of 50 mM TRIS buffer at pH 8.8 and 500M NaCl at 300 cm/h. The culture medium (20-30CV) is further loaded at 214 cm/h. the column is then washed with the equilibrating buffer (10CV) and immediately after with 100 mM Sodium Acetate pH4.0 (10CV), at 300 cm/h. The product is then eluted at 300 cm/h with 100 mM Glycine HCl buffer at pH3.3.

Example 14

PPA HyperCel is conditioned with 3CV (column Volume) of 50 mM TRIS buffer at pH 8.8 and 500M NaCl at 300 cm/h. The culture medium (20-30CV) is further loaded at 214 cm/h. the column is then washed with the equilibrating buffer (10CV) and immediately after with 100 mM Sodium Acetate pH4.0 (10CV), at 300 cm/h. The product is then eluted at 300 cm/h with 75 mM Glycine HCl buffer at pH3.3.

Example 15

PPA HyperCel is conditioned with 3CV (column Volume) of 50 mM TRIS buffer at pH 8.8 and 500M NaCl at 300 cm/h. The culture medium (20-30CV) is further loaded at 214 cm/h. the column is then washed with the equilibrating buffer (10CV) and immediately after with 100 mM Sodium Acetate pH4.0 (10CV), at 300 cm/h. The product is then eluted at 300 cm/h with 50 mM Glycine HCl buffer at pH3.3.

Example 16

PPA HyperCel is conditioned with 3CV (column Volume) of 50 mM TRIS buffer at pH 8.8 and 500M NaCl at 300 cm/h. The culture medium (20-30CV) is further loaded at 214 cm/h. the column is then washed with the equilibrating buffer (10CV) and immediately after with 100 mM Sodium Acetate pH4.0 (10CV), at 300 cm/h. The product is then eluted at 300 cm/h with 100 mM Glycine HCl buffer at pH3.1.

Example 17

PPA HyperCel is conditioned with 3CV (column Volume) of 50 mM TRIS buffer at pH 8.8 and 500M NaCl at 300 cm/h. The culture medium (20-30CV) is further loaded at 214 cm/h. the column is then washed with the equilibrating buffer (10CV) and immediately after with 100 mM Sodium Acetate pH4.0 (10CV), at 300 cm/h. The product is then eluted at 300 cm/h with 50 mM Glycine HCl buffer at pH3.1

TABLE 4

Summary of operating parameters of examples 10-17
Operating Parameters for PPA HyperCel column

| Purification Procedures | Example | Parameter | Target Range | % recovery BMP |
|---|---|---|---|---|
| Equilibration | 10-17 | Flow Rate | 300 cm/h | |
| | 10-17 | Conductivity | 50 mS/cm | |
| | 10-17 | pH | 8.9 ± 0.2 | |
| Load | 10-17 | Flow Rate | 214 cm/h | |
| | 10-17 | Conductivity | 50 mS/cm | |
| | 10-17 | pH | 8.9 ± 0.2 | |
| Wash | 10-17 | Flow Rate | 300 cm/h | |
| Elution | 10-17 | Flow Rate | 300 cm/h | |

TABLE 5

Summary of elution results of examples 10-17
Results for Elution of PPA HyperCel column

| Example | Glycine concentration (mM) | pH | Yield (RP-HPLC) | Purity (RP-HPLC) |
|---|---|---|---|---|
| 10 | 200 | 3.5 | 50 | 81 |
| 11 | 125 | 3.5 | 44 | 90 |
| 12 | 75 | 3.5 | 30 | 100 |
| 13 | 100 | 3.3 | 86 | 84 |
| 14 | 75 | 3.3 | 81 | 84 |
| 15 | 50 | 3.3 | 60 | 89 |
| 16 | 100 | 3.1 | 64 | 83 |
| 17 | 50 | 3.1 | 44 | 92 |

Example 18

PPA HyperCel is conditioned with 3CV (column Volume) of 50 mM TRIS buffer at pH 8.9 and 500M NaCl at 152 cm/h. The culture medium (12.5CV) is further loaded at 152 cm/h. the column is then washed with the equilibrating buffer (5CV) and immediately after with, 25 mM Sodium Phosphate pH7.4 (5CV) and further with 100 mM Sodium Acetate pH4.0 (10CV), at 152 cm/h. The product is then eluted at 152 cm/h with 100 mM Glycine HCl buffer at pH2.7.

Example 19

PPA HyperCel is conditioned with 3CV (column Volume) of 50 mM TRIS buffer at pH 8.9 and 500M NaCl at 152 cm/h. The culture medium (25CV) is further loaded at 152 cm/h. the column is then washed with the equilibrating buffer (5CV) and immediately after with, 25 mM Sodium Phosphate pH7.4 (5CV) and further with 100 mM Sodium Acetate pH4.0 (10CV), at 152 cm/h. The product is then eluted at 152 cm/h with 100 mM Glycine HCl buffer at pH2.7.

Example 20

PPA HyperCel is conditioned with 3CV (column Volume) of 50 mM TRIS buffer at pH 8.9 and 500M NaCl at 152 cm/h. The culture medium (50CV) is further loaded at 152 cm/h. the column is then washed with the equilibrating buffer (5CV) and immediately after with, 25 mM Sodium Phosphate pH7.4 (5CV) and further with 100 mM Sodium Acetate pH4.0 (10CV), at 152 cm/h. The product is then eluted at 152 cm/h with 100 mM Glycine HCl buffer at pH2.7.

Example 21

PPA HyperCel is conditioned with 3CV (column Volume) of 50 mM TRIS buffer at pH 8.9 and 500M NaCl at 152 cm/h. The culture medium (100CV) is further loaded at 152 cm/h. the column is then washed with the equilibrating buffer (5CV) and immediately after with, 25 mM Sodium Phosphate pH7.4 (5CV) and further with 100 mM Sodium Acetate pH4.0 (10CV), at 152 cm/h. The product is then eluted at 152 cm/h with 100 mM Glycine HCl buffer at pH2.7.

TABLE 6

Summary of operating parameters of examples 18-21
Operating Parameters for PPA HyperCel column

| Purification Procedures | Example | Parameter | Target Range | % recovery BMP |
|---|---|---|---|---|
| Equilibration | 18-21 | Flow Rate | ≤152 cm/h | |
| | 18-21 | Conductivity | ≤50 mS/cm | |
| | 18-21 | pH | 8.9 ± 0.2 | |
| Load | 18-21 | Flow Rate | ≤152 cm/h | |
| | 18-21 | Conductivity | ≤50 mS/cm | |
| | 18-21 | pH | 8.9 ± 0.2 | |
| Wash | 18-21 | Flow Rate | ≤152 cm/h | |
| Elution | 18-21 | Flow Rate | ≤152 cm/h | |

TABLE 7

Summary of elution results of examples 18-21
Results for elution of PPA HyperCel column

| Example | Glycine concentration (mM) | pH | CV culture medium | % recovery BMP in elution |
|---|---|---|---|---|
| 18 | 100 | 2.7 | 12.5 | 98 |
| 19 | 100 | 2.7 | 25 | 98 |
| 20 | 100 | 2.7 | 50 | 98 |
| 21 | 100 | 2.7 | 100 | 80 |

Example 22

PPA HyperCel is scaled-up to 2 L of column and it is conditioned with 3CV (column Volume) of 50 mM TRIS buffer at pH 8.9 and 500M NaCl at 150 cm/h. The culture medium (25 L) is further processed to remove cells and debris and the pH and conductivity has been adjusted. The culture medium is loaded at 150 cm/h. the column is then washed with the equilibrating buffer (3CV) and immediately after with, 25 mM Sodium Phosphate pH7.4 (3CV) and further with 100 mM Sodium Acetate pH4.0 (8CV), at 150 cm/h. The product is then eluted at 150 cm/h with 100 mM Glycine HCl buffer at pH2.7 (6CV). The product is collected in the first 2.3CV of elution.

TABLE 8

Summary of example 22
Operating Parameters for PPA HyperCel column

| Purification Procedures | Example | Parameter | Target Range | % recovery BMP |
|---|---|---|---|---|
| Equilibration | 22 | Flow Rate | 150 cm/h | |
| | 22 | Conductivity | ≤50 mS/cm | |
| | 22 | pH | 8.9 ± 0.2 | |
| | 22 | volume | 1600-2200 ml | |
| Load | 22 | Flow Rate | 150 cm/h | |
| | 22 | pH | 8.9 ± 0.2 | |
| | 22 | Volume culture medium | 25 L | |
| | 22 | | | <2 |
| Wash | 22 | Flow Rate | 150 cm/h | |
| | 22 | | | <2 |
| Elution | 22 | Flow Rate | 150 cm/h | |
| | 22 | pH | 2.7 ± 0.2 | |
| | 22 | 2.3 CV | | ≥92 |
| | 22 | 3.7 CV | | ≤4 |

Examples First Eluate Processing

Example 23

First eluate, coming from the mixed-mode column, is inactivated by decreasing the pH with HCl 1.2%. v/v. The final pH must be included between 2.60 and 2.80. MLV (Murine Leukemia Virus, which is a retro-virus), reduction has been determined at pH 2.70 as VRF (Viral Reduction Factor) expressed as log reduction.

TABLE 9

Summary of example 23
MLV log reduction by pH inactivation

| Example | Residence time (min) | Titre/ml Run 1 | Titre/ml Run 2 | VRF ($\log_{10}$) Run 1 | VRF ($\log_{10}$) Run 2 |
|---|---|---|---|---|---|
| 23 | 1 | 1.73* | 1.73* | 6.63 ± 0.38 | ≥6.42 ± 0.33 |
| 23 | 30 | 1.73* | 1.73* | | |
| 23 | 60 | −0.52 | −0.05* | | |
| 23 | 120 | 1.73* | 1.73* | | |

*The Poisson distribution has been used to calculate the titre when no virus was detected in the sample.

Example 24

The solution is further processed before loading onto the cation exchange column. The BMP solution is added to one volume of a solution of 25 mM sodium phosphate dibasic pH 8.5-9.4 and 0.24% w/v of Tween 20 (polysorbate 20) under stirring condition (300 rpm). The pH is controlled during the addition and it is adjusted with a solution of 1M NaOH. The final pH is included between 7.2 and 7.6. the final Tweeen 20 concentration is about 0.12% w/v. The recovery of BMP is higher than 98%.

Example 25

The solution is further processed before loading onto the cation exchange column. The BMP solution is added to one volume of a solution of 25 mM sodium phosphate dibasic pH 8.5-9.4 and 0.5% w/v of Tween 20 (polysorbate 20) under stirring condition (300 rpm). The pH is controlled during the addition and it is adjusted with a solution of 1M NaOH. The final pH is included between 7.2 and 7.6. the final Tweeen 20 concentration is about 0.25% w/v. The recovery of BMP is higher than 98%.

Example 26

The solution is further processed before loading onto the cation exchange column. The BMP solution is added to one volume of a solution of 25 mM sodium phosphate dibasic pH 8.5-9.4 and 1.0% w/v of Tween 20 (polysorbate 20) under stirring condition (300 rpm). The pH is controlled during the addition and it is adjusted with a solution of 1M NaOH. The final pH is included between 7.2 and 7.6. the final Tweeen 20 concentration is about 0.5% w/v. The recovery of BMP is higher than 98%.

Tween 20 is a surfactant which shows an inactivation activity against MLV. The inactivation has been determined for the example 24 as VRF and the results are reported in table 10.

TABLE 10

MLV log reduction by Tween 20 inactivation

| Example | Residence time (min) | Titre/ml Run 1 | Titre/ml Run 2 | VRF ($\log_{10}$) Run 1 | VRF ($\log_{10}$) Run 2 |
|---|---|---|---|---|---|
| 24 | 1 | 5.93 | 6.02 | 4.88 ± 0.41 | 4.34 ± 0.34 |
| 24 | 50 | 4.10 | 4.27 | | |
| 24 | 100 | 3.25 | 3.00 | | |
| 24 | 260 | 1.14 | 1.59 | | |

Examples Cation Exchange Column

Example 27

CM Sepharose (volume=5 ml) is conditioned with 3CV (column Volume) of 25 mM sodium Phosphate buffer at pH 7.4 at 230 cm/h. The processed first eluate is loaded at 230 cm/h. The column is further washed with the equilibrating buffer (3CV) and immediately after with 25 mM Sodium Phosphate pH7.0 and 300 mM sodium chloride (10CV) at 230 cm/h. The product is then eluted at 230 cm/h with 50 mM TRIS HCl buffer pH8.9 and 500 mM sodium chloride (6CV). The product is collected in the first 2CV of elution.

Example 28

CM Sepharose (volume=5 ml) is conditioned with 3CV (column Volume) of 25 mM sodium Phosphate buffer at pH 7.4 at 230 cm/h. The processed first eluate is loaded at 230 cm/h. The column is further washed with the equilibrating buffer (3CV) and immediately after with 25 mM Sodium Phosphate pH7.4 and 150 mM sodium chloride (10CV) at 230 cm/h. The product is then eluted at 230 cm/h with 50 mM TRIS HCl buffer pH8.9 and 500 mM sodium chloride (6CV). The product is collected in the first 2CV of elution.

Example 29

CM Sepharose (volume=5 ml) is conditioned with 3CV (column Volume) of 25 mM sodium Phosphate buffer at pH 7.4 at 230 cm/h. The processed first eluate is loaded at 230 cm/h. The column is further washed with the equilibrating buffer (3CV) and immediately after with 50 mM TRIS HCl buffer pH8.9 and 150 mM sodium chloride (5CV) at 230 cm/h. The product is then eluted at 230 cm/h with 50 mM TRIS HCl buffer pH8.9 and 500 mM sodium chloride (6CV). The product is collected in the first 2CV of elution.

TABLE 11

Summary of examples 27-29
Operating Parameters for CM Sepharose column

| Purification Procedures | Example | Parameter | Target Range | % recovery BMP |
|---|---|---|---|---|
| Equilibration | 27, 28, 29 | Flow Rate | 230 cm/h | |
| | 27, 28, 29 | Conductivity | ≤5 mS/cm | |
| | 27, 28, 29 | pH | 7.4 ± 0.2 | |
| | 27, 28, 29 | volume | 3 CV | |
| Load | 27, 28, 29 | Flow Rate | 230 cm/h | |
| | 27, 28, 29 | pH | 7.4 ± 0.2 | |
| | 27, 28, 29 | Volume | 200 CV | |
| | 27, 28, 29 | | | <5 |
| Wash | 27 | Flow Rate | 230 cm/h | <5 |
| | 28 | Flow Rate | 230 cm/h | <5 |
| | 29 | Flow Rate | 230 cm/h | <10 |
| Elution | 27, 28, 29 | Flow Rate | 230 cm/h | |
| | 27, 28, 29 | pH | 8.9 ± 0.2 | |
| | 27, 28 | | | >90 |
| | 29 | 2 CV | | >80 |

Example 30

CM Sepharose (volume=25 ml) is conditioned with 3CV (column Volume) of 25 mM sodium Phosphate buffer at pH 7.4 at 230 cm/h. The processed first eluate is loaded at 230 cm/h. The column is further washed with the equilibrating buffer (3CV) and immediately after with 50 mM TRIS HCl buffer pH8.9 (10CV) at 230 cm/h. The product is then eluted at 230 cm/h with 50 mM TRIS HCl buffer pH8.9 and 200 mM sodium chloride (6CV). The product is collected in the first 4CV of elution.

TABLE 12

Summary of example 30
Operating Parameters for CM Sepharose column

| Purification Procedures | Example | Parameter | Target Range | % recovery BMP |
|---|---|---|---|---|
| Equilibration | 30 | Flow Rate | 230 cm/h | |
| | 30 | Conductivity | ≤5 mS/cm | |
| | 30 | pH | 7.4 ± 0.2 | |
| | 30 | volume | 3 CV | |
| Load | 30 | Flow Rate | 230 cm/h | |
| | 30 | pH | 7.4 ± 0.2 | |
| | 30 | Volume | 800 CV | |
| | 30 | | | <5 |
| Wash | 30 | Flow Rate | 230 cm/h | <10 |
| Elution | 30 | Flow Rate | 230 cm/h | |
| | 30 | pH | 8.9 ± 0.2 | |
| | 30 | 4 CV | | >80 |
| | 30 | RP-HPLC purity | 99% | |
| | 30 | aggregates | 5-15% | |

Example 31

CM Sepharose (volume=500 ml) is conditioned with 3CV (column Volume) of 25 mM sodium Phosphate buffer at pH 7.4 at 230 cm/h. The processed first eluate is loaded at 230 cm/h. The column is further washed with the equilibrating buffer (10CV) and immediately after with 50 mM TRIS HCl buffer pH8.9 (10CV) at 230 cm/h. The product is then eluted at 230 cm/h with 50 mM TRIS HCl buffer pH8.9 and 200 mM sodium chloride (6CV). The product is collected in the first 4CV of elution.

Example 32

CM Sepharose (volume=300 ml) is conditioned with 3CV (column Volume) of 25 mM sodium Phosphate buffer at pH 7.4 at 230 cm/h. The processed first eluate is loaded at 230 cm/h. The column is further washed with the equilibrating buffer (10CV) and immediately after with 25 mM sodium phosphate buffer pH7.4 and 150 mM Arginine (10CV) at 230 cm/h. The product is then eluted at 230 cm/h with 50 mM TRIS HCl buffer pH8.9 and 200 mM sodium chloride (6CV). The product is collected in the first 4CV of elution.

TABLE 13

Summary of examples 31-32
Operating Parameters for CM Sepharose column

| Purification Procedures | Example | Parameter | Target Range | % recovery BMP |
|---|---|---|---|---|
| Equilibration | 31, 32 | Flow Rate | 245 cm/h | |
| | 31, 32 | Conductivity | ≤5 mS/cm | |
| | 31, 32 | pH | 7.4 ± 0.2 | |
| | 31, 32 | volume | 3 CV | |
| Load | 31, 32 | Flow Rate | 245 cm/h | |
| | 31, 32 | pH | 7.4 ± 0.2 | |
| | 31, 32 | Volume | 800 CV | |
| | 31, 32 | | | <5 |
| Wash | 31 | Flow Rate | 245 cm/h | |
| | 31 | pH | 8.9 ± 0.2 | <40 |
| | 31 | Flow Rate | 245 cm/h | |

TABLE 13-continued

Summary of examples 31-32
Operating Parameters for CM Sepharose column

| Purification Procedures | Example | Parameter | Target Range | % recovery BMP |
|---|---|---|---|---|
| | 32 | pH | 7.4 ± 0.2 | <10 |
| Elution | 31, 32 | Flow Rate | 245 cm/h | |
| | 31, 32 | pH | 8.9 ± 0.2 | |
| | 31 | 4 CV | | >50 |
| | 32 | 4 CV | | >80 |
| | 31 | RP-HPLC purity | 99% | |
| | 31 | aggregates | 5-15% | |
| | 31 | Host Cell Proteins | <20000 ppm | |
| | 32 | RP-HPLC purity | 99% | |
| | 32 | aggregates | 5-25% | |
| | 32 | Host Cell Proteins | <20000 ppm | |

Examples Second Eluate Processing

Example 33

The second eluate, coming from the cation exchange column, is diluted with 5 volumes of water for injection to achieve a sodium chloride concentration of 40 mM.

Example 34

The second eluate, coming from the cation exchange column, is diafiltered by TFF cassette (MWCO=30000 Da) to remove the 99% of sodium chloride.

TABLE 14

Summary of experimental condition of example 34
Operating Parameters for TFF dia-filtration

| Example | Parameter | Target Range |
|---|---|---|
| 34 | Pressure Feed | 1.4-1.6 bar |
| 34 | Pressure Retentate | 0.8-1.0 bar |
| 34 | Pressure Permeate | 0.0 bar |
| 34 | TMP | 1.0-1.3 bar |
| 34 | Flow Rate Retentate | 3.9 ± 0.2 L/h |
| 34 | Flow Rate Permeate | 0.8 ± 0.1 L/h |

Example 35

The second eluate, coming from the cation exchange column, is diluted with 3.5 volumes of 50 mM TRIS pH 8.9 and 100 mM Arginine to achieve a sodium chloride concentration of about 60 mM and an Arginine concentration of 70 mM.

Examples Anion Exchange Column

Example 36

DEAE Sepharose (volume=5 ml) is conditioned with 3CV (Column Volume) of 50 mM TRIS buffer at pH 8.9 at 230 cm/h. The processed second eluate, as in the example 33, is loaded at 230 cm/h. The column is further washed with the equilibrating buffer (10CV) at 230 cm/h. The product is then eluted at 230 cm/h with 50 mM TRIS HCl buffer pH8.9 and 150 mM sodium chloride (6CV).

Example 37

DEAE Sepharose (volume=5 ml) is conditioned with 3CV (Column Volume) of 50 mM TRIS buffer at pH 8.9 at 230 cm/h. The processed second eluate, as in the example 33, is loaded at 230 cm/h. The column is further washed with the equilibrating buffer (10CV) at 230 cm/h and with 25 mM sodium phosphate pH 7.4 (5CV) at the same linear flow rate. The product is then eluted at 230 cm/h with 25 mM sodium phosphate pH 7.4 and 100 mM sodium chloride buffer (6CV).

Example 38

DEAE Sepharose (volume=5 ml) is conditioned with 3CV (Column Volume) of 50 mM TRIS buffer at pH 8.9 at 230 cm/h. The processed second eluate, as in the example 34, is loaded at 230 cm/h. The column is further washed with the equilibrating buffer (10CV) at 230 cm/h. The product is then eluted at 230 cm/h with 50 mM TRIS HCl buffer pH8.9 and 150 mM sodium chloride (6CV).

TABLE 15

Summary of operating parameters of examples 36-38
Operating Parameters for DEAF Sepharose column

| Purification Procedures | Example | Parameter | Target Range | % recovery BMP |
|---|---|---|---|---|
| Equilibration | 36, 37, 38 | Flow Rate | 230 m/h | |
| | 36, 37, 38 | Conductivity | ≤10 mS/cm | |
| | 36, 38 | pH | 8.9 ± 0.2 | |
| | 37 | pH | 7.4 ± 0.2 | |
| | 36, 37, 38 | volume | 3 CV | |
| Load | 36, 37, 38 | Flow Rate | 230 cm/h | |
| | 36, 38 | pH | 8.9 ± 0.2 | |
| | 37 | pH | 7.4 ± 0.2 | |
| | 36, 37, 38 | Volume | 15 CV | |
| | 36, 37, 38 | | | <5 |
| Wash | 36, 37, 38 | Flow Rate | 230 cm/h | |
| | 36, 38 | pH | 8.9 ± 0.2 | <40 |
| | 37 | pH | 7.4 ± 0.2 | |
| | 36, 37, 38 | Conductivity | ≤5 mS/cm | <10 |
| Elution | 36, 37, 38 | Flow Rate | 230 cm/h | |
| | 36, 38 | pH | 8.9 ± 0.2 | |
| | 37 | pH | 7.4 ± 0.2 | |
| | 36, 37, 38 | 6 CV | | |
| | 36 | | | <40 |
| | 36 | RP-HPLC purity | 99% | |
| | 36 | aggregates | 0-2% | |
| | 36 | Host Cell Proteins | <5000 ppm | |
| | 37 | | | <40 |
| | 37 | RP-HPLC purity | 99% | |
| | 37 | aggregates | 0-2% | |
| | 37 | Host Cell Proteins | <5000 ppm | |
| | 38 | | | <25 |
| | 38 | RP-HPLC purity | 99% | |
| | 38 | aggregates | 0-2% | |
| | 38 | Host Cell Proteins | <5000 ppm | |

Example 39

CaptoQ is conditioned with 3CV (Column Volume) of 50 mM TRIS buffer at pH 8.9 and 100 mM Arginine at 245 cm/h. The processed second eluate, as in the example 35, is loaded at 245 cm/h. The column is further washed with the equilibrating buffer (10CV), 25 mM sodium phosphate pH7.4 (7CV), 25 mM sodium phosphate pH6.5 and 75 mM sodium chloride (7CV) and, once again with 25 mM sodium phosphate pH7.4 (7CV) at 245 cm/h. The product is then eluted at 245 cm/h with PBS 1.5× buffer pH7.4 (5CV).

TABLE 16

Summary of example 39
Operating Parameters for captoQ column

| Purification Procedures | Example | Parameter | Target Range | % recovery BMP |
|---|---|---|---|---|
| Equilibration | 39 | Flow Rate | 230 m/h | |
| | 39 | Conductivity | ≤10 mS/cm | |
| | 39 | pH | 8.9 ± 0.2 | |
| | 39 | volume | 3 CV | |
| Load | 39 | Flow Rate | 230 cm/h | |
| | 39 | pH | 8.9 ± 0.2 | |
| | 39 | Volume | 15 CV | |
| | 39 | | | <5 |
| Wash | 39 | Flow Rate | 230 cm/h | |
| 50 mM TRIS pH8.9, 100 mM Arginine | 39 | pH | 8.9 ± 0.2 | <1 |
| 25 mM sodium phosphate pH7.4 | 39 | pH | 7.4 ± 0.2 | <1 |
| 25 mM sodium phosphate pH7.4, 75 mM NaCl | 39 | pH | 6.5 ± 0.2 | <1 |
| 25 mM sodium phosphate pH7.4 | 39 | pH | 7.4 ± 0.2 | <1 |
| Elution | 39 | Flow Rate | 230 cm/h | |
| | 39 | pH | 7.4 ± 0.2 | |
| | 39 | CV02: from 0 to 2 | | <30 |
| | 39 | CV25: from 2 to 5 | | <60 |
| | 39 (CV02) | RP-HPLC purity | 99% | |
| | 39 (CV02) | aggregates | 0-5% | |
| | 39 (CV02) | Host Cell Proteins | <25000 ppm | |
| | 39 (CV25) | RP-HPLC purity | 99% | |
| | 39 (CV25) | aggregates | 0-1% | |
| | 39 (CV25) | Host Cell Proteins | <5000 ppm | |

The invention claimed is:

1. A method of purifying a secreted TGF-β superfamily protein, wherein the secreted TGF-β superfamily protein is a bone morphogenetic protein (BMP), said method comprising:
   i. contacting a solution containing the secreted TGF-β superfamily protein with a Hydrophobic Charge Interaction Chromatography (HCIC) resin for obtaining a first eluate containing the TGF-β superfamily protein, wherein the first eluate containing the secreted TGF-β superfamily protein is eluted from the HCIC resin using an elution Glycine buffered solution; and
   ii. contacting the first eluate containing the secreted TGF-β superfamily protein with a cation-exchange chromatography resin for obtaining a second eluate containing the secreted TGF-β superfamily protein.

2. The method according to claim 1 further comprising
   iii. contacting the second eluate containing the secreted TGF-β superfamily protein with an anion-exchange chromatography resin for obtaining the purified secreted TGF-β superfamily protein.

3. The method according to claim 1 wherein the secreted TGF-β superfamily protein is BMP-4.

4. The method according to claim 1 wherein the HCIC resin is a mixed-mode resin carrying as ligands n-hexylamine (HEA) or phenylpropylamine (PPA) or 4-Mercapto-Ethyl-Pyridine (4-MEP).

5. The method according to claim 1 wherein the solution containing the secreted TGF-β superfamily protein is that obtained from a harvest cell culture medium, containing the protein of interest, which has been filtered and adjusted to pH 7.0-9.5 and NaCl concentration of 250-800 mM.

6. The method according to claim 5 wherein the cell is a mammalian cell.

7. The method according to claim 1 wherein subsequent to loading the solution containing the secreted TGF-β superfamily protein onto the HCIC resin, the HCIC resin is subjected to at least two washing steps preformed respectively with a washing buffer (A) at neutral pH 6.5-7.5 and with a washing buffer (B) at pH 3.0-4.5; and an elution step performed with a Glycine buffered solution at pH 2.5-3.5 with glycine concentration of 50 mM to 200 mM.

8. The method according to claim 1 wherein the cation exchange resin is a weak cation exchange resin.

9. The method according to claim 2 wherein the anion exchange resin is a strong anion exchange resin.

10. The method according to claim 7, wherein the washing buffer (A) is a solution of sodium phosphate buffer, potassium phosphate buffer, TRIS buffer, Bis-TRIS, HEPES buffer or MES buffer, and the washing buffer (B) is a solution of Sodium Acetate buffer, Sodium Phosphate buffer, Potassium Phosphate buffer, Lactic acid or Citric acid having a concentration of 50-250 mM.

11. A method of purifying a secreted TGF-β superfamily protein, said method comprising:
   contacting a solution containing the secreted TGF-β superfamily protein with a Hydrophobic Charge Interaction Chromatography (HCIC) resin; and
   eluting the secreted TGF-β superfamily protein from the HCIC resin using a glycine elution buffer, thereby purifying the secreted TGF-β superfamily protein.

* * * * *